(12) United States Patent
Wang et al.

(10) Patent No.: US 8,878,093 B2
(45) Date of Patent: Nov. 4, 2014

(54) METHOD AND APPARATUS FOR INSPECTING ADHESIVE QUALITY

(75) Inventors: Pei-Chung Wang, Troy, MI (US); Zongqing Lin, Shanghai (CN); Xinmin Lai, Shanghai (CN); Yansong Zhang, Shanghai (CN); Guanlong Chen, Shanghai (CN)

(73) Assignee: GM Global Technology Operations LLC, Detroit, MI (US)

( * ) Notice: Subject to any disclaimer, the term of this patent is extended or adjusted under 35 U.S.C. 154(b) by 1578 days.

(21) Appl. No.: 12/180,950

(22) Filed: Jul. 28, 2008

(65) Prior Publication Data

US 2010/0019785 A1    Jan. 28, 2010

(51) Int. Cl.
*B23K 11/00* (2006.01)
*B23K 11/11* (2006.01)
*G01N 27/04* (2006.01)
*B23K 11/25* (2006.01)

(52) U.S. Cl.
CPC ............ *B23K 11/115* (2013.01); *G01N 27/048* (2013.01); *B23K 11/256* (2013.01); *B23K 11/257* (2013.01); *B23K 11/258* (2013.01)
USPC .... 219/117.1; 219/91.1; 219/91.2; 219/91.21

(58) Field of Classification Search
USPC .......... 219/85.14, 85.15, 86.23, 86.41, 86.51, 219/109, 110, 91, 92, 93, 94, 117.1, 118; 148/516, 523, 527, 535
See application file for complete search history.

(56) References Cited

U.S. PATENT DOCUMENTS

| | | | | |
|---|---|---|---|---|
| 3,350,536 A | * | 10/1967 | Frederick et al. | 219/92 |
| 4,028,522 A | * | 6/1977 | Chihoski et al. | 219/109 |
| 4,675,494 A | * | 6/1987 | Dilay | 219/91.21 |
| 5,194,709 A | * | 3/1993 | Ichikawa et al. | 219/109 |
| 5,245,293 A | * | 9/1993 | Runner | 324/663 |
| 6,359,249 B1 | * | 3/2002 | Brown et al. | 219/86.51 |
| 6,903,298 B2 | * | 6/2005 | Wang et al. | 219/110 |
| 2001/0045413 A1 | * | 11/2001 | Suita | 219/86.51 |
| 2005/0217785 A1 | * | 10/2005 | Hable et al. | 156/60 |
| 2007/0214623 A1 | * | 9/2007 | Lee et al. | 29/25.35 |

* cited by examiner

*Primary Examiner* — Thien S Tran
(74) *Attorney, Agent, or Firm* — Quinn Law Group, PLLC

(57) ABSTRACT

A method and apparatus inspect a quality of an adhesive material used for joining a pair of work surfaces during a weld-bonding process. A pair of work pieces are at least partially bonded by a layer of the adhesive material, and the dynamic displacement of one or both electrodes is measured through a duration of the resistance welding process to determine relative moisture content of the adhesive. A control action is executed when the dynamic displacement exceeds a stored threshold value. The apparatus includes a welding device having a pair of electrodes for providing a clamping force and an electrical current necessary for forming the welded joint, a sensor for measuring a dynamic displacement of at least one of the pair of electrodes and/or another portion of the welding device during formation of the welded joint. A controller has an algorithm for determining a relative moisture using the dynamic displacement.

13 Claims, 3 Drawing Sheets

METHOD AND APPARATUS FOR INSPECTING ADHESIVE QUALITY

TECHNICAL FIELD

The present invention relates to a method and an apparatus for inspecting the quality of an adhesive material used for bonding adjacent work pieces in conjunction with resistance welding in a weld-bonding process.

BACKGROUND OF THE INVENTION

Various methods exist for joining two or more metal sheets, panels, or "work pieces" when manufacturing a vehicle or other metal-based products. Typically, such metal work pieces are fused or welded together using a controlled application of intense heat and pressure, with the heat being directed at or along an interface, seam, or joint between adjacent work pieces. While some welding techniques utilize a high-temperature arc in forming the welded joint, other welding techniques apply pressure to the work pieces in order to generate heat using the inherent resistivity or electrical resistance of the metal work pieces. Such a process is referred to generally as "resistance welding".

Spot welding is one of the more common types of resistance welding techniques, wherein opposing electrodes apply a clamping force on a set of adjacent work pieces while an electrical current is directed through the work pieces. The electrical resistance of the metallic materials forming the work pieces generates intense localized heating, which coupled with the clamping force exerted by the electrodes or welding tips, ultimately melts or fuses the work pieces to form a weld "nugget". This nugget is positioned within the work pieces themselves, with the external surfaces of a properly formed spot welded joint appearing as a depression or indentation in the surfaces of the work pieces.

Resistance welding techniques such as spot welding can be used in conjunction with a layer of adhesive material which is first applied between the work pieces prior to formation of the joint. The adhesive material provides a portion of the final holding or bond strength. In certain applications, the adhesive material may be cured using any localized heat generated during the resistance welding process. The resultant welded joint is typically stronger than a purely spot-welded joint due to the bonding strength provided by the adhesive material. Moreover, use of the adhesive material can potentially reduce the number of required spot welds for a given application, potentially reducing the overall cost and efficiency of the manufacturing process.

Because of the potential cost and efficiency benefits of weld-bonding relative to traditional resistance welding techniques, modern manufacturing processes are beginning to use weld-bonding more frequently than in the past. However, weld-bonded joints rely heavily on the consistency and integrity of the adhesive material that is used for joining the work pieces. Such adhesive material is commonly epoxy-based, a material which can absorb humidity or moisture from the atmosphere when left exposed in the work environment. When the relative humidity is high, the strength of the joint will usually decline over time. As a result, a weld-bonding process that is employed in a relatively low-humidity environment can produce a welded joint having characteristics that are potentially inconsistent with those of a similar welded joint formed using an otherwise identical weld-bonding process, but formed within a relatively high-humidity environment.

SUMMARY OF THE INVENTION

Accordingly, a method and an apparatus are provided for inspecting a quality of an adhesive material used for joining two or more adjacent work pieces in conjunction with a weld-bonding process. Various measurements are taken during a resistance welding process. These values are compared to calibrated threshold values to determine an estimated or a relative moisture content of the adhesive material, a value which ultimately affects the bonding strength of the adhesive material. In this manner, the presence of adhesive material which has been overly exposed to humidity or moisture can be detected in-process without requiring direct testing of the adhesive material itself, and/or without resorting to destructive testing of the welded joint after the joint is formed and cured. However, such off-line testing processes may still be used to validate the results generated by the apparatus and method the invention.

In particular, the method includes determining whether the adhesive material has a relative moisture content which exceeds an acceptable threshold or limit by measuring, calculating, or otherwise determining a relative or approximate resistance value, i.e., a resistivity, of the adhesive material. In one embodiment, such a resistance value can be directly determined by measuring or calculating the resistance value. Or, it can be indirectly determined by measuring a dynamic expansion and contraction, i.e., the "dynamic displacement", of the work pieces forming a work assembly. Dynamic displacement can be measured directly by measuring and recording any movement of a suitable portion of a welding device, such as a robotic arm, electrodes, etc., and/or by calculating or measuring the resistance value of the adhesive material. In another embodiment, the resistance value can be determined via a measured depth of an indentation formed by the electrodes at the locus of the welded joint. Measurements of the indentation can indirectly determine the dynamic displacement which coincided with the indentation, with the measurements being determined in various ways, such as by using calipers or a laser measurement device.

The apparatus itself includes a weld-bonding machine or device having an electrical supply, such as a hardwired connection to an electrical outlet, a battery, or another ready source of electrical energy. The apparatus also includes a pair of electrodes forming a set of welding tips, at least one sensor, and a controller operable for executing an algorithm or a method. The sensor or sensors measure values corresponding to the formation of the welded joint, such as any electrical current and/or voltage level supplied to, and/or any dynamic displacement of, the electrodes used to form a welded joint between two work pieces in a weld-bonding process.

The method includes comparing the values, such as the dynamic displacement measurements, to stored or calibrated ranges or thresholds, and then executing an appropriate control action when one or more of the values exceed the calibrated threshold. Control actions can include, for example, the illumination of an external device configured as a warning lamp or audio alarm, sending a control message to a server or another external device, and/or executing any other appropriate control action, such as shutting down the welding machine or welding process to allow for inspection and/or replacement of the adhesive material, inspection/testing of the welded joint, etc. In this manner, the relative moisture content of the adhesive material can be determined in real-time, that is, while the manufacturing process is active, to thereby optimize the quality of the resultant welded joint.

The above features and advantages and other features and advantages of the present invention are readily apparent from the following detailed description of the best modes for carrying out the invention when taken in connection with the accompanying drawings.

DESCRIPTION OF THE PREFERRED EMBODIMENTS

Figure 1:
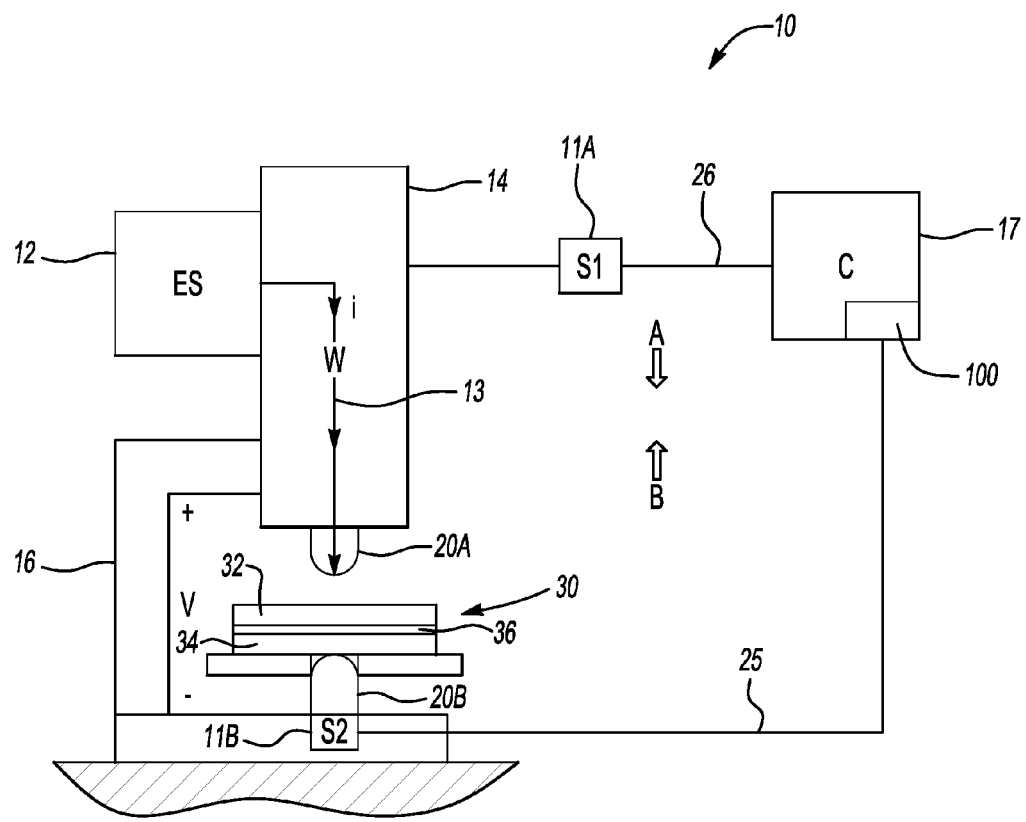
FIG. 1 is a schematic illustration of an apparatus for determining a relative moisture content of adhesive material used in a weld-bonding process.

Referring to the drawings wherein like reference numbers represent like components throughout the several figures, and beginning with FIG. 1, a resistance welding apparatus 10 includes a resistance welding machine, robot, or device (W) 14 which is electrically connected to an energy supply (ES) 12. The energy supply 12 can be any source of electrical energy, such as a hardwired connection to an electrical panel (not shown), a battery, a generator, or any other suitable energy source that is operable for delivering an electrical current (i) through a conductor 13 positioned within or along the welding device 14.

The ES 12 provides the necessary levels of electrical voltage and current for fusing or welding a work assembly 30. As used herein, the term "work assembly" refers to any pair of metal-based panels, sheets, pieces, or other metallic work surfaces which are to be weld-bonded together, i.e., permanently attached or joined via a combination of an adhesive material 36 (see FIGS. 2A-C) and resistance welding. The welding device 14 can be configured as any resistance welding robot, machine, or other device capable of generating the required levels of resistive heat and a concurrent clamping force for forming a suitable welded joint, such as in the exemplary case of a conventional spot welding process as described below with reference to FIGS. 2A-C.

Figures 2A, 2B, 2C:
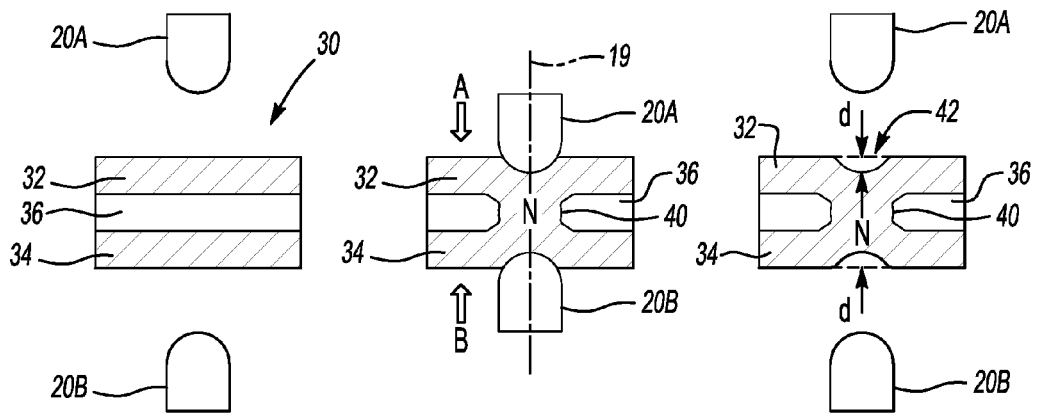
FIG. 2A is a schematic illustration of a pair of representative work pieces prior to formation of a welded joint via a resistance welding process.
FIG. 2B is a schematic illustration of the work pieces of FIG. 2A during formation of the welded joint.
FIG. 2C is a schematic illustration of the work pieces of FIGS. 2A and 2B after formation of the welded joint.

The welding device 14 includes a pair of electrodes 20A, 20B configured as a pair of opposing welding tips. The electrode 20A is moveable toward the work assembly 30 in the direction of arrow A. The electrodes 20A, 20B apply a clamping force to the work assembly 30, and electrical current (arrow i) then flows from the ES 12 through the conductor 13 to the electrode 20A. The current (arrow i) then passes through the work assembly 30 to the electrode 20B. The resistance at the faying interfaces of the adhesive material 36 and the workpieces 32, 34 (see FIGS. 2A-C) of the work assembly 30, and the resistivity of the materials forming the work assembly 30 to the electrical current (arrow i) passing therethrough, together form intense localized heat within the work assembly, ultimately melting a portion of each of the work pieces 32, 34 (see FIGS. 2A-2C) forming the work assembly 30 in order to form a "nugget" (N) 40 within the work assembly 30, as shown in FIG. 2B. The electrodes 20A, 20B then move away from each other, with the electrode 20B moving in the direction of arrow A and the electrode 20A moving in the direction of arrow B, allowing the work assembly 30 to be repositioned in preparation for a subsequent process step, such as the formation of another welded joint, painting, heat curing, etc.

The apparatus 10 as shown in the exemplary embodiment of FIG. 1 includes a C-frame or a support 16 that is adjacent to the work assembly 30. Typically, the electrode 20B is stationary and the electrode 20A is moveable, although other configurations can be used within the scope of the invention, such as a scissor gun wherein both electrodes 20A, 20B are moveable. The support 16 can be either fixed or stationary with respect to the work assembly 30 when the work assembly 30 moves as part of an automated manufacturing process, or the support 16 may itself be moveable with respect to a stationary or moving work assembly 30. That is, the support 16 can be configured as a component of a welding robot having seven axes of movement, as will be understood by those of ordinary skill in the art, in order to provide the desired freedom of movement with respect to the work assembly 30 being constructed.

Sensors 11A and 11B, which are also respectively labeled S1 and S2 in FIG. 1 for clarity, are connected to the welding device 14 and to the electrodes 20A, 20B, respectively. The sensors 11A, 11B are operable for measuring, detecting, or otherwise determining a particular electrical and/or mechanical value or values related to the formation of a weld in the work assembly 30. In particular, the sensor 11A is operable for determining a value or values describing the dynamic initial thermal expansion and subsequent thermal contraction, i.e., the dynamic displacement of the electrodes 20A, 20B or weld tips. The dynamic displacement can be determined by measuring the movements of the electrodes 20A and/or 20B in response to the expansion, melting, and formation of the nugget 40 (see FIGS. 2B and 2C) during weld-bonding. The sensors 11A, 11B relay or transmit a signal 26, 25 respectively to an electronic control unit or controller 17 for use by an algorithm or method 100 stored therein or accessible thereby, with the method 100 being discussed below with reference to FIG. 4.

For example, dynamic displacement can include a distance or range of motion of the electrodes 20A, 20B as the electrodes 20A, 20B move generally in the direction of arrows B and A as needed during the welding process. Such motion can include any or all of a distance of motion by the electrode 20A as material within the work assembly 30 melts during weld formation, and as the work assembly 30 moves or gives at or along the locus of the weld under a clamping force applied by the electrodes 20A, 20B. The motion can also include initial movement of the electrodes 20A, 20B in the directions of arrows A and B, respectively, after the electrodes 20A, 20B begin passing current (arrow i) through the work assembly 30. Maximum initial movement of electrode 20A in the direction of arrow B and electrode 20B in the direction of arrow A due to thermal expansion of the work assembly 30 can be referred to as the "initial peak", and is the result of an initial temperature-induced expansion of the work assembly 30 before the metal inside the work assembly 30 begins to melt.

The controller 17 is also operable for determining, whether directly or indirectly via measurement and/or calculation or a look-up table, an electrical resistance of the work assembly 30. For example, the sensors 11A, 11B can measure the current represented by the arrow i and a voltage (V) between the electrodes 20A, 20B, and the controller 17 can utilize a lookup table (not shown) or the formula $R=V/I$ to determine the resistance of the work assembly 30. The resistance of the adhesive material in particular can be determined by subtracting known values of the resistance of the work pieces 32, 34 (see FIGS. 2A-C), and the resistance at the faying interfaces of the adhesive material 36 and the workpieces 32, 34. Alternately, the sensor 11A and/or 11B, or another external sensor (not shown) can be configured to directly or indirectly measure the depth of any resultant depression or indentation 42 (see FIG. 2C) formed by the electrodes 20A, 20B. That is, the depth "d" of the indentation 42 of FIG. 2C can be measured or determined using a gauge, a caliper, a laser measurement device, etc.

Referring to FIGS. 2A-C, the work assembly 30 of FIG. 1 is shown in FIG. 2A prior to initiation of a resistance welding process, shown here as an exemplary spot welding process. The work assembly 30 includes an upper work piece 32 and a lower work piece 34, separated by a layer of adhesive material 36 of the type known in the art. The work assembly 30 is positioned between the electrodes 20A, 20B. In FIG. 2B, the electrodes 20A, 20B are clamped or forced onto the work assembly 30. The adhesive material 36, which is usually an electrical insulator, is forced away from a primary axis 19 of the electrodes 20A, 20B, i.e., away from the locus of the weld cap. Electrical current (arrow i) flows through the work piece 32, through the now immediately adjacent work piece 34, and into the electrode 20B. The resistivity of the work pieces 32, 34 and the resistance at the faying interfaces of the adhesive material 36 and the workpieces 32, 34 causes a portion of the metal of the work pieces 32, 34 to melt and fuse in the form of the nugget 40. In FIG. 2C, the electrodes 20A, 20B are once again in their initial positions, leaving an indentation 42 having a depth "d" in each of the work pieces 32, 34.

Figure 3:
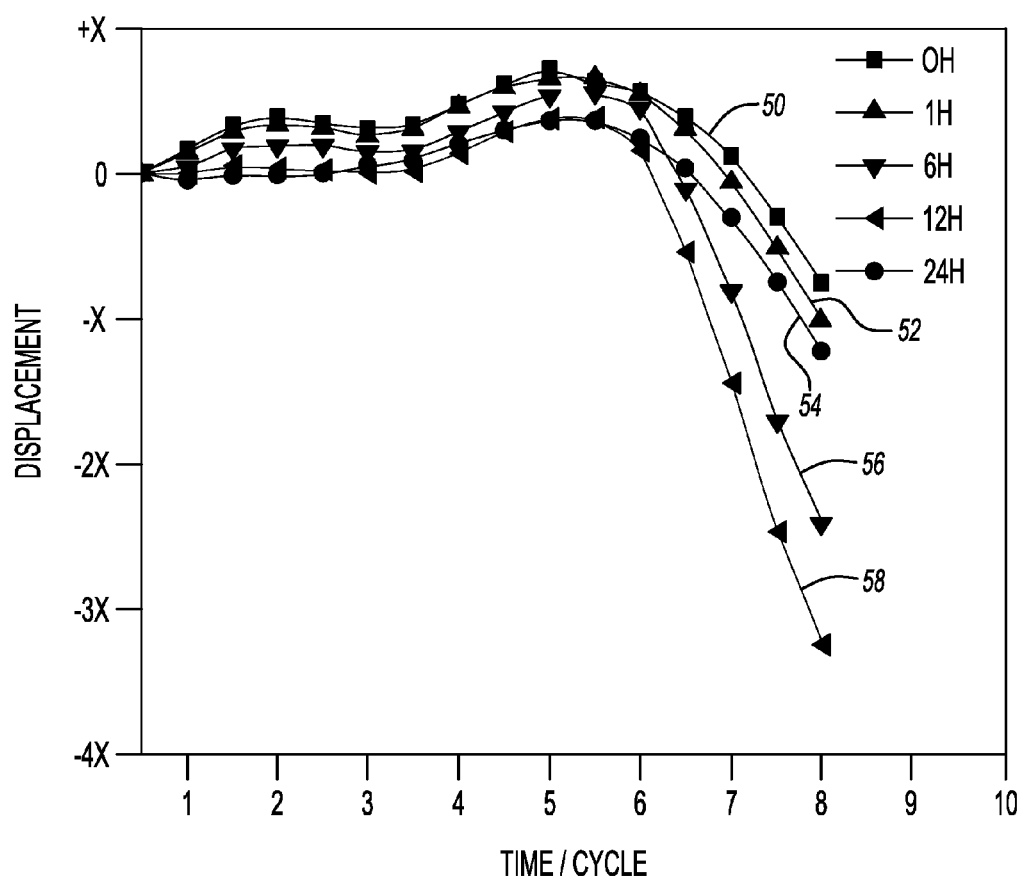
FIG. 3 is a graph depicting the relationship between dynamic displacement of an electrode portion of a welding machine and exposure time of the adhesive.

Referring to FIG. 3, a representative set of traces 50, 52, 54, 56, and 58 describe the effects of moisture or humidity on the performance of the adhesive material 36 of FIGS. 2A-C. Typical adhesives used in weld-bonding processes are composed at least partially by epoxy, a material which has an affinity for moisture. The adhesive material 36 is ordinarily an excellent insulator when positioned between the conductive layers of the work pieces 32 and 34 of FIGS. 2A-C. However, as the adhesive material absorbs moisture over time, the insulating or resistive property of the adhesive material declines. The relationship between heat (H), electrical current (I), resistance (R), and time (t) can be represented by the equation:

$$H = I^2 \cdot R \cdot t$$

Therefore, as the resistivity (R) of the adhesive drops in conjunction with its absorption of moisture, less heat (H) is generated at the faying interfaces of the workpieces 32, 34, potentially resulting in a welded joint having less than optimal qualities.

In FIG. 3, the trace 50 represents a baseline displacement of one or both electrodes 20A, 20B of FIG. 1 as a weld-bonded joint is being formed. For a given thin gage steel sheet (e.g., 0.8 mm), a typical spot weld takes approximately 8 to 10 cycles to form, i.e., an interval of approximately 130 to 160 milliseconds. The trace 50 therefore represents a representative level of dynamic displacement of a portion of the welding device 14 of FIG. 1, such as the electrodes 20A and/or 20B, over this interval. Trace 52 represents the same adhesive material 36 after it has been exposed for one hour within a humid environment prior to formation of a welded joint.

Likewise, trace 54 represents the dynamic displacement of the same portion of the welding device 14 of FIG. 1 after an exposure time of 6 hours. After approximately 6 hours of exposure, dynamic displacement begins to increase dramatically, as shown by the traces 56 and 58 which represent 12 hours and 24 hours of exposure, respectively. Therefore, it is possible to utilize a composite set of measurements describing the dynamic displacement of the welding device 14 as described above to determine a relative moisture content of the adhesive material 36 of FIGS. 2A-C. One possible method for doing so is shown in FIG. 4.

Figure 4:
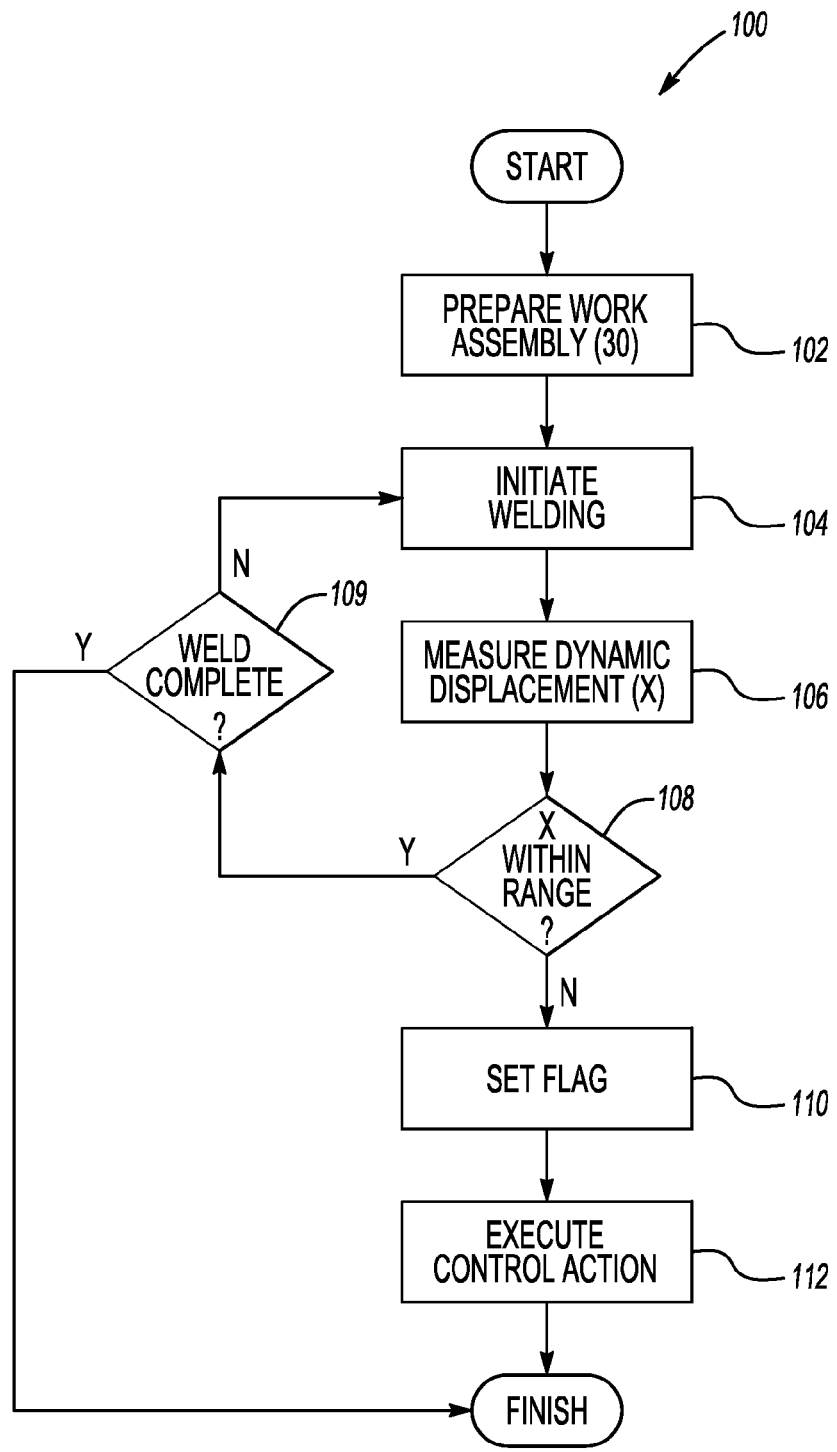
FIG. 4 is a flow chart describing an algorithm or a method that is usable in conjunction with the apparatus of FIG. 1.

Referring to FIG. 4, the algorithm or method 100 of FIG. 1 begins with step 102, wherein the work assembly 30 of FIGS. 1 and 2A-C is prepared for resistance welding. Step 102 includes applying a layer or layers of the adhesive material 36 of FIGS. 2A-C to one or both of the work pieces 32, 34, and then positioning the work pieces 32 and/or 34 as needed to properly orient the work pieces 32, 34 for the resistance welding process to follow. The method 100 then proceeds to step 104.

At step 104, resistance welding is initiated as described above with reference to FIGS. 2A-C. That is, electrical current and voltage is transmitted to the electrodes 20A, 20B as the electrodes 20A, 20B apply a clamping force to the work assembly 30. As this is occurring, the method 100 proceeds to step 106.

At step 106, the dynamic displacement (X) is measured, detected, or otherwise determined using the sensors 11A and/or 11B of FIG. 1. Step 106 can include directly measuring any thermal expansion and contraction of the work assembly 30, i.e., of the work pieces 32, 34 of FIGS. 2A-C, as the welded joint is being formed.

Step 106 can also or alternately include direct or indirect measurement of the depth "d" of the indentation 42 of FIG. 2C, as described above. Likewise, the step 106 can include the direct measurement of, or a calculation or estimate of, the resistance value or resistivity of the adhesive layer 36 of FIGS. 2A-C, which can be used to determine and/or validate any measurements describing the dynamic displacement (X). The method 100 then proceeds to step 108.

At step 108, the method 100 includes comparing the measurements of step 106 to a corresponding calibrated threshold value or values, such as a set of values previously recorded in or accessible by the controller 17 of FIG. 1. The calibrated threshold values can be determined using various methods, such as but not limited to destructively testing a set of welded joints formed using adhesive materials having known moisture contents. As will be understood by those of ordinary skill in the art, some dynamic displacement is unavoidable, and depending on the particular application, acceptable or threshold levels of dynamic displacement may vary widely. If the dynamic displacement is determined at step 108 to be within the allowable thresholds, the method 100 proceeds to step 109. Otherwise, the method 100 proceeds to step 110.

At step 109, the method 100 includes determining whether the welded joint is complete. If so, the method 100 is finished, resuming with step 102 for any subsequent welded joint formation. If the welded joint is not complete, the method 100 repeats step 104.

At step 110, a flag is set indicating to the controller 17 that dynamic displacement, or any other values determined at step 106 pertaining thereto, are not within an allowable range, i.e., that the dynamic displacement measured or determined at step 106 exceeds a calibrated threshold value. Depending on the variance of the values from the threshold, different flags might be set within the scope of the invention. For example, minor deviations from the threshold might require only minor control actions, and could receive a flag value of "1". A severe deviation from the threshold might require the welding process to be shutdown, and could receive a flag value of "2". After setting an appropriate flag, the method 100 then proceeds to step 112.

At step 112, the method 100 includes executing a control action in response to the particular flag that was set at step 110. Control actions can include anything that is appropriate under the circumstances, such as but not limited to: adding more spot welds to compensate for adhesive degradation, activating an audio and/or visual indicator or alarm, sending an electronic message to a data acquisition system or other computing device, automatically shutting down a process to allow time for inspection of the adhesive material 36 of FIGS. 2A-C, overriding the flag set at step 110, etc. Step 112 may also include testing, such as destructive or non-destructive testing, actual moisture content testing or measurement, and/or dimensional measurement of the nugget 40 of FIGS. 2B and 2C, or any other required strength or quality testing of the resultant welded joint. Data from such validation or verification testing can then be used to update any stored threshold values, as needed.

While the best modes for carrying out the invention have been described in detail, those familiar with the art to which this invention relates will recognize various alternative designs and embodiments for practicing the invention within the scope of the appended claims.

The invention claimed is:

1. A method for determining a relative moisture content of an adhesive material that is used for joining a pair of work surfaces of a pair of work pieces in conjunction with a resistance welding process utilizing a pair of electrodes, the method comprising:
   using the resistance welding process to form a welded joint between the pair of work pieces, the pair of work pieces being at least partially separated by a layer of the adhesive material to form a work assembly;
   determining a resistance value corresponding to an electrical resistivity of the adhesive material during the resistance welding process, including measuring a current and a voltage between the pair of electrodes, calculating a resistance of the work assembly using the measured current and voltage, and subtracting from the calculated resistance a known resistance of the pair of work pieces;
   determining the relative moisture content of the adhesive material during the resistance welding process using the determined electrical resistivity; and
   executing a control action when, during the resistance welding process, the determined relative moisture content of the adhesive material exceeds a stored relative moisture threshold value.

2. The method of claim 1, wherein determining the resistance value includes measuring a dynamic displacement corresponding to a thermal expansion and contraction of the pair of work surfaces during formation of the welded joint.

3. The method of claim 2, wherein measuring the dynamic displacement includes measuring a depth of an indentation formed by the pair of electrodes in the pair of work surfaces.

4. The method of claim 2, wherein measuring the resistance value includes at least one of directly measuring and calculating the electrical resistivity of the adhesive material.

5. The method of claim 1, wherein the resistance welding process is a spot-welding process.

6. The method of claim 1, wherein executing a control action includes at least one of: activating an indicator or an alarm, sending an electronic message to an external system, and shutting down the resistance welding process.

7. A method for determining a relative moisture content of a welded joint during a weld-bonding process, the method comprising:
   measuring a value corresponding to a dynamic displacement of a pair of electrodes during the weld-bonding process, including measuring a movement of the pair of electrodes caused by the thermal expansion of the pair of work surfaces during formation of the welded joint;
   determining the relative moisture content during the weld-bonding process using the measured value corresponding to the dynamic displacement; and
   executing a control action when, during the weld-bonding process, the relative moisture exceeds a stored relative moisture threshold value.

8. The method of claim 7, wherein executing a control action includes testing one of a strength of the welded joint and an actual moisture content of an adhesive material used in the formation of the welded joint.

9. The method of claim 7, wherein executing a control action includes at least one of: forming additional spot welds, activating an indicator or an alarm, sending an electronic message to an external system, and shutting down the weld-bonding process.

10. The method of claim 7, wherein measuring a value corresponding to a dynamic displacement of a pair of electrodes includes measuring a distance between the pair of electrodes.

11. An apparatus for determining a relative moisture content of an adhesive material used in forming a welded joint between a pair of adjacent work pieces during a weld-bonding process, the apparatus comprising:
   a welding device having a pair of electrodes operable for providing a clamping force and an electrical current necessary for forming the welded joint;
   at least one sensor connected to the pair of electrodes and configured to measure a dynamic displacement of at least one of the pair of electrodes during formation of the welded joint; and
   a controller in communication with the sensor, wherein:
      the controller determines a relative moisture content of the adhesive material during execution of the weld-bonding process using the measured dynamic displacement and a resistance value of the adhesive material to an electrical current as the electrical current passes between the pair of electrodes during formation of the welded joint; and
      executes a control action when, during the execution of the weld-bonding process, the relative moisture content exceeds a threshold relative moisture value.

12. The apparatus of claim 11, wherein the welding device is a spot-welding device, and wherein the pair of adjacent work pieces are a pair of sheet metal portions of a vehicle.

13. The apparatus of claim 11, wherein the control action is selected from the group consisting of: activating an indicator or an alarm, testing the welded joint, sending an electronic message to an external system, and shutting down the weld-bonding process.

* * * * *